(12) United States Patent
Szeto

(10) Patent No.: US 7,251,642 B1
(45) Date of Patent: Jul. 31, 2007

(54) ANALYSIS ENGINE AND WORK SPACE MANAGER FOR USE WITH GENE EXPRESSION DATA

(75) Inventor: Ernest Szeto, Berkeley, CA (US)

(73) Assignee: Gene Logic Inc., Gaithersburg, MD (US)

( * ) Notice: Subject to any disclaimer, the term of this patent is extended or adjusted under 35 U.S.C. 154(b) by 296 days.

(21) Appl. No.: 10/213,881

(22) Filed: Aug. 6, 2002

Related U.S. Application Data

(60) Provisional application No. 60/309,909, filed on Aug. 6, 2001, provisional application No. 60/309,906, filed on Aug. 6, 2001.

(51) Int. Cl.
*G06F 7/00* (2006.01)
*G01N 33/48* (2006.01)

(52) U.S. Cl. .......................... 707/1; 702/19
(58) Field of Classification Search .............. 702/19, 702/22; 707/1
See application file for complete search history.

(56) References Cited

U.S. PATENT DOCUMENTS

| | | | |
|---|---|---|---|
| 5,495,606 A | 2/1996 | Borden et al. |
| 5,569,580 A | 10/1996 | Young |
| 5,589,337 A | 12/1996 | Farr |
| 5,634,053 A | 5/1997 | Noble et al. |
| 5,692,107 A | 11/1997 | Simoudis et al. |
| 5,702,915 A | 12/1997 | Miyamoto |
| 5,736,354 A | 4/1998 | Fielden et al. |
| 5,769,074 A | 6/1998 | Barnhill et al. |
| 5,787,425 A | 7/1998 | Bigus |
| 5,811,231 A | 9/1998 | Farr et al. |
| 5,835,755 A | 11/1998 | Stellwagen, Jr. |
| 5,873,083 A | 2/1999 | Jones et al. |
| 5,933,818 A | 8/1999 | Kasravi et al. |
| 6,109,776 A | 8/2000 | Haas |
| 6,128,608 A | 10/2000 | Barnhill |
| 6,160,105 A | 12/2000 | Cunningham et al. |
| 6,185,561 B1 | 2/2001 | Balaban et al. |
| 6,189,013 B1 | 2/2001 | Maslyn et al. |
| 6,203,987 B1 | 3/2001 | Friend et al. |
| 6,223,186 B1 | 4/2001 | Rigault et al. |
| 6,308,170 B1 | 10/2001 | Balaban |

(Continued)

OTHER PUBLICATIONS

Paton et al., Bioinformatics, vol. 16, pp. 548-557, 2000.*

(Continued)

*Primary Examiner*—Cheyne D. Ly
(74) *Attorney, Agent, or Firm*—Eleanor M. Musick; Procopio, Cory, Hargreaves & Savitch LLP

(57) ABSTRACT

A platform is for managing, integrating, and analyzing gene expression data. The platform includes a Run Time Engine (RTE) which provides more direct, quicker, and more efficient access to gene expression data through the use of memory mapped files. The platform also includes a workspace that is implemented in directories with data objects comprising XML descriptors coupled with binary data objects for storing gene and sample identifiers and input parameters for saved analysis sessions. The platform provides various Application Programming Interfaces (APIs) to a data warehouse, including a low-level C++ API, a high-level C++ API, a Perl API, R API, and CORBA API to access gene expression data from RTE memory mapped files. These APIs offer quicker and more direct access to the memory, thus improving the speed of overall operations.

27 Claims, 8 Drawing Sheets

U.S. PATENT DOCUMENTS

| | | |
|---|---|---|
| 6,309,822 B1 | 10/2001 | Fodor et al. |
| 6,408,308 B1 | 6/2002 | Maslyn et al. |
| 6,418,382 B2 | 7/2002 | Rothberg et al. |
| 6,427,141 B1 | 7/2002 | Barnhill |
| 6,453,241 B1 | 9/2002 | Bassett, Jr. et al. |
| 6,470,277 B1 | 10/2002 | Chin et al. |
| 6,484,183 B1 | 11/2002 | Balaban et al. |
| 6,532,462 B2 | 3/2003 | Balaban |

OTHER PUBLICATIONS

Barillot et al., Bioinformatics, vol. 15, pp. 157-169, 1999.*
Stoeckert et al., Bioinformatics, vol. 17, pp. 300-308, 2001.*
Kimball, R., The Data Warehouse Toolkit, John Wiley & Sons, Inc., 1996.*
Ramakrishnan R., Database Management Systems, WCB/McGraw-Hill, 1998.*
Light, R., Presenting XML, Sams.net Publishing, 1997.*
Dodge et al., Essential Oracle8i Data Warehousing, John Wiley & Sons, Inc., pp. 439-446 and 704, 2000.*
Spellman et al., Molecular Biology of the Cell, vol. 9, pp. 3273-3297, 1998.*
Hornik K., R FAQ, Version 1.2-46, Free Software Foundation, Inc., pp. 1-38, Apr. 2001.*
Brazma et al., FEBS, pp. 17-24, 2000.*
Bassett, D., Jr., et al., "Gene Expression Informatics—It's All in Your Mine," Nature Genetics Supplement, vol. 21, Jan. 1999, pp. 51-55.
Canfield, K., et al., "Mapping XML Documents into Databases: A Data-Driven Framework for Bioinformatic Data Interchange," AMIA Symposium, Nov. 2000, pp. 121-125.
Duggan, D., et al., "Expression Profiling Using cDNA Microarrays," Nature Genetics Supplement, vol. 21, Jan. 1999, pp. 10-14.
Ermolaeva, O., et al., "Data Management and Analysis for Gene Expression Arrays," Nature Genetics Supplement, vol. 20, Sep. 1998, pp. 19-23.
Rebhan, M., et al., "GeneCards: A Novel Functional Genomics Compendium with Automated Data Mining and Query Reformulation Support," Bioinformatics, vol. 14, No. 8, 1998, pp. 656-664.
Tarczy-Hornoch, P., et al., "GeneClinics: A Hybrid Text/Data Electronic Publishing Model Using XML Applied to Clinical Genetic Testing," J. Amer. Med. Inform. Assoc., vol. 7, No. 3, 2000, pp. 267-276.

* cited by examiner

```xml
<?xml version="1.0"?>
<Sample_Template_Data xmlns:xsi="http://www.w3.org/2001/XMLSchema-instance"
xsi:noNamespaceSchemaLocation="sample.xsd">

<Study id="Gene Logic Study 1234">
    <name>GL1234</name>
    <description>Control Rat study</description>
    <investigator>John Doe</investigator>
</Study>

<Study_Group id="Rat No Treatment 001">
    <name>Rat No Treatment</name>
    <description>Control rats given no treatment</description>
    <comments />
    <study ref="Gene Logic Study 1234" />
    <set_of_proprietary_data>
        <proprietary_data>
            <tag>Gene_Logic_Study_Group_Name</tag>
            <value>Gene Logic Study Group GL1234 - No Treatment Rats</value>
        </proprietary_data>
    </set_of_proprietary_data>
</Study_Group>

<Study_Group id="Rat Control Treatment 002">
    <name>Rat Control Treatment</name>
    <description>Control rats treated with corn oil</description>
    <comments />
    <study ref="Gene Logic Study 1234" />
    <set_of_proprietary_data>
        <proprietary_data>
            <tag>Gene_Logic_Study_Group_Name</tag>
            <value>Gene Logic Study Group GL1234 - Control Rats</value>
        </proprietary_data>
    </set_of_proprietary_data>
</Study_Group>

<Donor id="Rat-A">
    <name>Rat-A</name>
    <disease>Normal</disease>
    <animal_strain />
    <human_race />
    <comments>comments</comments>
    <age>
        <value>15</value>
        <unit>weeks</unit>
    </age>
</Donor>

<Sample id="Rat-A Liver No Treatment">
    <name>Rat-A No Treatment</name>
    <source />
    <organ>Liver, NOS</organ>
    <disease>Normal</disease>
    <comments />
    <pooled_id />
    <study ref="Gene Logic Study 1234" />
    <donor ref="Rat-A" />
    <study_group ref="Rat No Treatment 001" />
    <type>Tissue</type>
    <harvest_time />
    <species>
        <genus>Rattus</genus>
        <species>norvegicus</species>
    </species>
    <cell_line />
    <set_of_proprietary_data>
        <proprietary_data>
            <tag>Gene_Logic_Study_Group_Name</tag>
            <value>Gene Logic Study Group GL1234 - No Treatment Rats</value>
        </proprietary_data>
    </set_of_proprietary_data>
</Sample>

<Treatment id="T1">
    <description>no treatment control</description>
    <agent>none</agent>
    <regimen />
    <route />
    <solvent />
    <sample ref="Rat-A Liver No Treatment" />
    <dosing />
    <time>
        <value>120</value>
        <unit>minutes</unit>
    </time>
</Treatment>
```

Fig. 5

ANALYSIS ENGINE AND WORK SPACE MANAGER FOR USE WITH GENE EXPRESSION DATA

CROSS-REFERENCE TO RELATED APPLICATIONS

This application claims priority to U.S. provisional application Ser. No. 60/309,906 and provisional patent application Ser. No. 60/309,909, both filed Aug. 6, 2001 and both of which are incorporated herein by reference. This application is related to each of application Ser. No. 09/862,424, filed May 23, 2001, which claims priority to U.S. provisional application Ser. No. 60/206,571, filed May 23, 2000, Ser. No. 10/090,144, filed Mar. 5, 2002, which claims priority to provisional application Ser. No. 60/325,776, filed Mar. 5, 2001, and Ser. No. 10/096,645, filed Mar. 14, 2002, which claims priority to U.S. provisional application Ser. No. 60/275,465, filed Mar. 14, 2001. This application is related to PCT application Serial No. US02/19877, filed in the U.S. Receiving Office on Jun. 24, 2002, which claims priority to provisional application Ser. No. 60/299,741, filed Jun. 22, 2001. Each of the related applications is incorporated herein by reference in its entirety for all purposes.

FIELD OF THE INVENTION

The present invention relates generally to systems and methods for integrating, managing, and a computer platform for storing, organizing and retrieving biological information and more specifically to a platform for management and searching of gene expression data and related information from multiple data sources data by multiple users. According to another aspect, the invention relates generally to systems and methods which store gene expression data in efficient memory mapped files, and the storage of gene (Affymetrix® fragment) and sample identifiers, as well as input parameters to saved analysis sessions, comprised of XML files with large binary attachments.

BACKGROUND

The study of gene expression brings valuable information to the researcher about cellular function that can be applied directly to drug discovery and development. Devices and computer systems have been developed for collecting information about gene expression or expressed sequence tag ("EST") expression in large numbers of tissues.

DNA microarrays are glass or nylon chips or substrates containing arrays of DNA samples, or "probes," which can be used to analyze gene expression. A fluorescently labeled nucleic acid is brought into contact with the microarray and a scanner generates an image file indicating the locations within the microarray at which the labeled nucleic acids are bound. Based on the identity of the probes at these locations, information such as the monomer sequence of DNA or RNA can be extracted. By profiling gene expression, transcriptional changes can be monitored through organ and tissue development, microbiological infection, and tumor formation. The robotic instruments used to spot the DNA samples onto the microarray surface allow thousands of samples to be simultaneously tested. This high-throughput approach increases reproducibility and production.

Microarray technologies enable the generation of vast amounts of gene expression data. Effective use of these technologies requires mechanisms to manage and explore large volumes of primary and derived or analyzed gene expression data. Furthermore, the value of examining the biological meaning of the information is enhanced when set in the context of sample profiles and gene annotation data. The format and interpretation of the data depend strongly on the underlying technology. Hence, exploring gene expression data requires mechanisms for integrating gene expression data across multiple platforms and with sample and gene annotations.

The GeneChip® Probe Array of Affymetrix, Inc. of Santa Clara, Calif. is one example of a widely-adopted microarray technology that provides for the high-volume screening of samples for gene expression. Affymetrix® also offers a series of software solutions for data collection, conversion to AADM™ ("Affymetrix® Analysis Data Model") database format, data mining and a multi-user laboratory information management system ("LIMS"). LIMS is a microarray data management package for users who are generating large quantities of GeneChip® Probe Array data. Data are published to a GATC™ ("Genetic Analysis Technology Consortium")-standard database which can be searched by mining tools that are GATC-compliant. The Affymetrix® technology has become one of the standards in the field, and large databases of gene expression data generated using this technology, along with associated information, have been assembled and are publicly-available for data mining by pharmaceutical, biotechnology and other researchers and clinicians. However, these researchers often have proprietary gene expression data, also generated using the Affymetrix® technology, and associated data which they may wish to compare with the existing database for validation, or to combine with the database for expanded searching. Further, the researchers may wish to utilize a specific analysis and visualization tool, or to use multiple such tools for comparison. Accordingly, a system is needed for integrating data from multiple sources and providing multiple options for analyzing the results.

As is apparent from the description above, the study of gene expression entails analyzing vast amounts of gene expression data, which can become very difficult to manage. One major problem in managing information that links gene expression data to biological function is the need to seamlessly integrate terabytes of information and to gather information under a wide variety of conditions. Additionally, all of this information may be translated into a common format. The sheer size of the database requires specific hardware and software capabilities that are not usually available to pharmaceutical and academic researchers. The problem of differing formats poses a separate challenge; it is somewhat like developing programs that can simultaneously work with millions of files saved in hundreds of file formats on thousands of Macintosh@, Unix, Linux, Windows®, and other types of computer systems.

Many pharmaceutical researchers and academic researchers need to somehow link gene expression information, clinical data, and the published literature in order to get meaningful leads about the basis of disease and good therapeutic approaches. In some cases, the gene expression information is available commercially, but the information is not immediately useful because it lacks the clinical information from source samples that connects biological functions with expression levels. As a result, researchers must work with a combination of commercial and academic resources and try to pull the results together. Since the information can exist in incompatible formats or be based on experiments conducted under widely varying conditions, the data can be difficult or impossible to manage.

An additional challenge in analyzing the vast amount of data is the time involved in managing and processing the gene expression data. For example, loading, transforming, and validating gene expression data into databases consumes a considerable amount of time and is typically performed after regular business hours. The need to perform these tasks after hours necessarily results in a period of time when users are unable to perform any study of gene expression data. Another challenge is with providing access to gene expression data to multiple users. When an analysis is performed which involves a set of gene expression data, that gene expression data is often inaccessible to other users. Because gene expression data is typically large in size, an analysis or study of gene expression data often ties up system resources in accessing the data, analyzing the data, and then presenting and managing the results of the analysis. A need exists for more efficient ways of managing gene expression data.

Another difficulty in managing the vast amount of data is that much of the data is binary data. This binary data is in a format that is rather efficient in terms of storage space but is rather inflexible and inconvenient. The binary data is efficient and enables faster processing since it contains low overhead usage of data bytes. On the other hand, the binary data is inflexible and is not readily portable to other formats, such as for use between Macintosh®, Unix, Linux, Windows® and other computer systems. This inflexibility is of particular concern with gene expression data since data may be derived from multiple sources of different formats, such as commercial, private sources, and even internal-derived proprietary data.

SUMMARY OF THE INVENTION

The invention addresses the problems above by providing platforms, systems, and methods for analyzing gene expression data. According to one aspect, a platform according to a preferred embodiment of the invention comprises a data warehouse for storing gene expression data and a Run Time Engine (RTE) for analyzing the gene expression data. The platform includes a plurality of application programming interfaces (APIs). A first API is a low-level API that is preferably programmed in C++. This first API provides relatively quick access to the gene expression data in the data warehouse. The platform includes user interfaces (UI's) which enable users to access the various tools associated with the platform for analyzing the gene expression data. A second API is interposed between the UIs and the first API and transfers requests for gene expression data from the U's to the first API.

The platform according to this embodiment of the invention provides integration, management, and analysis of large amounts of gene expression data from different sources. The platform provides for a faster and more efficient RTE for downloading data into an efficient file format which serves as the basis for analysis method computations in the gene expression data warehouse. The RTE is made faster and more efficient by providing code at a level closer to the machine level. Instead of relying solely on object-oriented constructs and using function calls, the RTE uses more direct accessing to the memory data structures in the analytical engine. The platform includes scripts and binaries to download data into memory mapped files. Further, the platform includes tools for cloning the memory mapped files to aid in customizing deployment data. In a preferred embodiment of the present invention, a C++ interface accesses the data as through memory mapped pointers. The computations supported by the RTE include the following methods: gene signature, gene signature differential, fold change, e-Northern, and contrast analysis. Other application programming interfaces built upon this low-level C++ API include, but are not limited to, a PERL API, a CORBA API, and an R API.

According to another aspect, gene expression data has a unique structure. The gene expression data includes a data object that contains the gene expression data. The data object is in a binary format and preferably comprises a large binary object (BLOB). The gene expression data also includes an eXtensible Mark-up Language (XML) descriptor for containing descriptive information on the binary object. The data object and XML descriptor are coupled together whereby the data object forms an attachment to the XML descriptor. The gene expression data also includes directory information specifying a directory where the data object is stored in the data warehouse.

With such a data structure, descriptive information concerning the data object, such as ownership, permissions, description, and gene chip set, can be accessed without having to access the bulk of the data. This data structure therefore provides the flexibility and portability of XML while maintaining the efficiency of the binary data structure. The workspace includes file path specifications, either relative or absolute, in the data objects. The file path specifications provide a more natural and efficient mapping into a file system, such as the Unix file system.

BRIEF DESCRIPTION OF THE DRAWINGS

The accompanying drawings, which are incorporated in and form a part of the specification, illustrate embodiments of the present invention and, together with the description, disclose the principles of the invention, wherein:

FIG. 5 is a portion of an exemplary XML sample data file;

DETAILED DESCRIPTION

Figure 1:
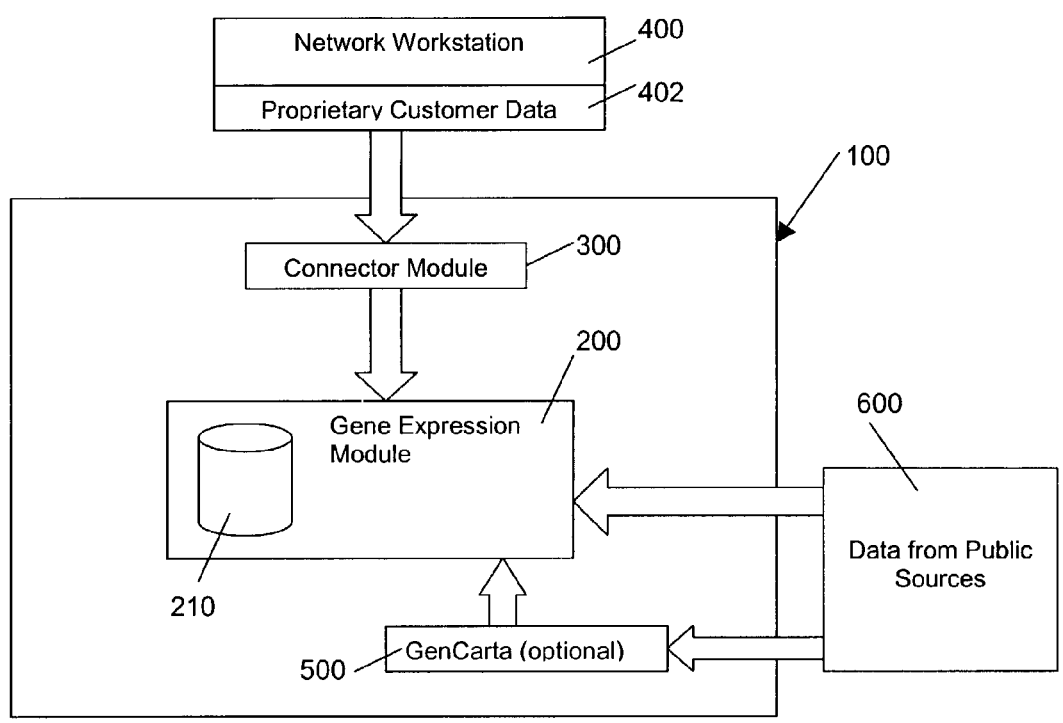
FIG. 1 is a block diagram of a top level view of a platform according to a preferred embodiment of the invention.

In general, with reference to FIG. 1, a platform 100 according to a preferred embodiment of the invention comprises an enterprise-wide platform 100 for gene expression research. In the exemplary embodiment, the platform 100 provides integration, management and analysis of large amounts of Affymetrix® GeneChip® Probe Array-based gene expression data from different sources. The platform 100 includes capabilities for capturing and analyzing associated clinical and experimental information. The platform 100 accepts data from the major Affymetrix® GeneChip® Probe Array types across various species and can accommodate custom chips.

As illustrated in FIG. 1, the platform 100 comprises a gene expression module 200, a connector module 300, and a user interface 400 comprising a network workstation, which includes means for entry of customer data 402. Optional module 500 provides access to the GenCarta™ transcriptome database system from Compugen, Ltd. of Tel Aviv, Israel. Both gene expression module 200 and the GenCarta system include means for extraction of data from public sources 600 such as Genbank, SwissProt, LocusLink, Unigene, KEGG, SPAD, PubMed, HUGO, OMIM, and GeneCard. This list is not intended to be exhaustive, and other sources, both private and public, may be used.

Figure 2:
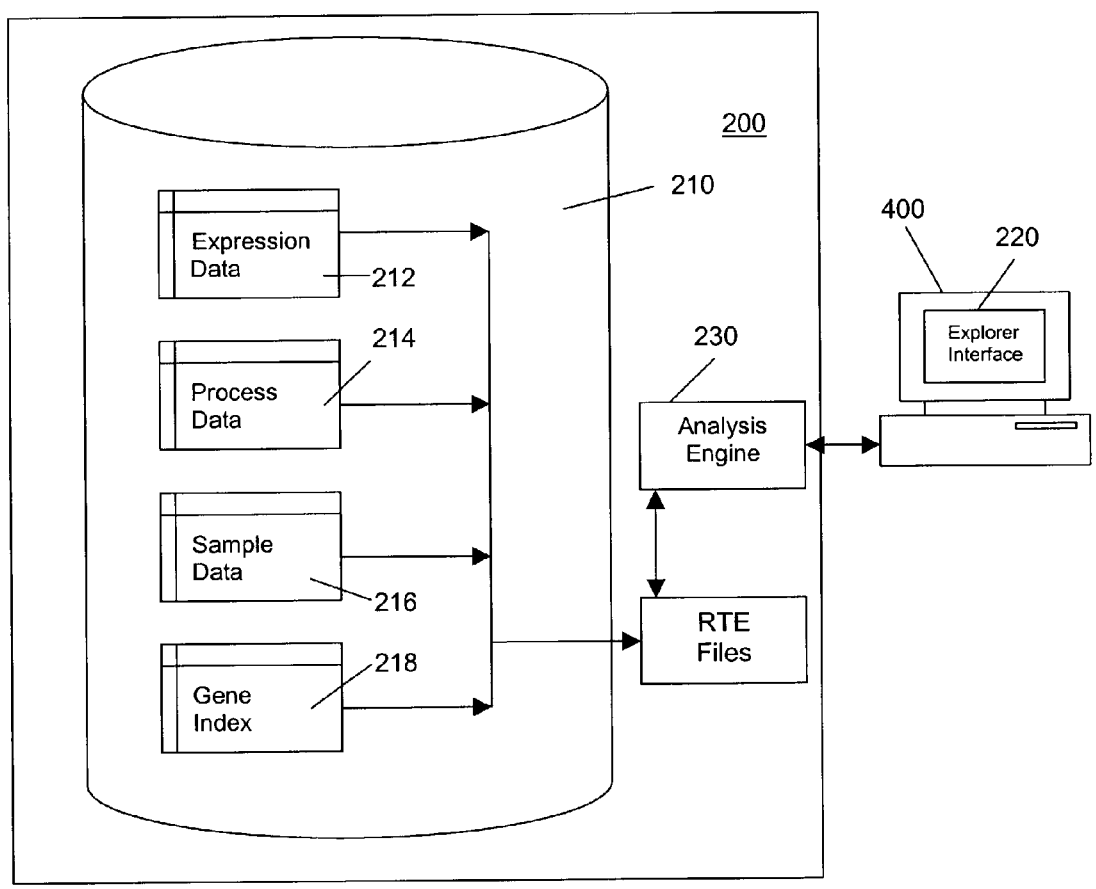
FIG. 2 is a block diagram of the gene expression module in the platform of FIG. 1.

Referring now to FIG. 2, gene expression module 200, available commercially as the GeneExpress® software system, comprises a three-tier client-server application with several sub-components. The data warehouse 210 is an Oracle®-based warehouse that maintains a large collection of data. Data warehouse 210 comprises summarized and curated gene expression data, integrated with sample and gene annotation data, and provides support for effective data exploration and mining. The data in the collection are partitioned into several databases. The gene expression database 212 contains a large volume of gene expression data in GATC/AADM compliant formats. Process database 214 stores information which characterizes and is related to the gene expression data in database 212, including information on experiment set grouping, QC data, and experimental conditions under which the gene expression data was generated. Sample database 216 stores sample or clinical data that include bio-samples, donors, and standardized terms that describe the samples. Sample data can be organized by static controlled vocabulary classes such as type, species, organ, clinical and demographic data, lifestyle factor, treatment outcome, etc., or can be organized into experimental study groups, SNOMED disease term and code, SNOMED organ term and code, etc. Templates are preferably used to standardize the organization of the sample data.

Gene index database 218 stores annotations which can be used to uniquely identify the gene expression data stored in database 212. The gene index database 218 links each gene fragment with existing annotations of the gene contained in public databases such as Genbank, SwissProt, LocusLink, Unigene, KEGG, SPAD, PubMed, HUGO, OMIM and GeneCard, all of which are known in the art. In linking the gene fragment with existing databases, the platform 100 maintains recognized biological meaning and identity, thus avoiding redundancy, ambiguity or errors. The gene fragments can also be linked in gene index database 218 to chromosomes and to biological pathways such as the protein signaling pathways available from BioCarta, Inc. of San Diego, Calif.

The partitioned databases are integrated and organized into a relational database for storing and retrieving biological information to support exploration and mining of gene expression data. The key objective of the relational database is to provide comprehensive access to gene expression and support for biological analysis. These objectives are obtained by the query capabilities that the relational database provides, as well as an application server that supports a biology-meaningful online analytical processor of the database data. This biology-meaningful online analytical processor examines large scale gene expression analysis of the data found in the relational database so as to reveal gene expression patterns that characterize certain functional states of the physiology of an organism. Operations supported by the application server include filtering, clustering, summarization, comparison and mapping onto pathways of gene expression data.

The functionality of the relational database, including its application server, is presented to users via the relational database user interface. In a preferred embodiment, the relational database user interface is provided in two formats, the first as a web application and the second as a Java client application.

The relational database, the application server, a client side user interface and a users' workspace database, preferably define a three-tier architecture to gene expression data and analysis. In a preferred embodiment, this system is integrated with an archive, an external file system that stores experimental data files and data for all experiments in the relational database.

The relational database is the repository of gene expression data produced by a genomics production pipeline. A relational database management system is the backbone data management infrastructure that supports the data flow of the production pipeline. The relational database management system is a complex, distributed heterogeneous system whose main components are interfaced by software modules enforcing well-defined protocols.

The main components of the relational database management system are: (1) a relational database management system; (2) a genomics production sample tracking system; (3) an application that documents the processes that generate the experimental files; (4) a software module that turns experimental files into a relational representation; and (5) a defect-inspecting software module.

The tissue repository information management system is an information system that supports the production cycle of a bio-repository, which support includes accessioning and inventory management of bio-samples, inputting pathology assessment and clinical data, and exporting of clinical data to the relational database for storing and retrieving biological information.

The genomics production sample tracking system consists of a collection of spread sheets which track samples as they move along the production pipeline. In another preferred embodiment, the application that documents the processes that generate the experimental files relates to the DAT, CEL and CHP files for each experiment. This process documentation is preferably stored in an Affymetrix database. This application minimizes data entry overhead.

In a preferred embodiment, the software module that turns experimental files into a relational representation supports several parallel publishing engines and also performs a list of consistency checks to ensure that the production standard operating procedure and publishing processes were executed successfully. This software module also preferably dumps the individual databases into text files (per table) and transfers them to a designated area in a staging UNIX server.

In another preferred embodiment, the defect-inspection module is a semi-automatic process in which chip images (DAT files) are inspected for defects that affect the quality of generated expression data. The result of this process are quality control reports, one per experiment, that are also migrated to the staging UNIX server.

The totality of these data streams defines the interface between the relational database management system and the relational database for storing and retrieving biological information. Specifically, all these data streams feed into a staging area where a warehouse building processes take place, i.e., validation, transformation and integration of the data.

Explorer interface 220 is a Java-based workspace application that provides the end-user interface to the system for user interface 400. User access to gene expression module 200 is limited to entry of search queries and a read-only function, which allows the user to view data stored in the data warehouse 210 that is identified as the result of the search. The explorer interface 220 provides analysis and visualization tools, and also provides seamless integration with other popular tools. Explorer interface 220 also keeps track of a user's research and analysis activities, including selected sample or gene sets and analysis results, for later retrieval through a workspace manager.

Analysis engine 230, also referred to as the "Run Time Engine" or "RTE," is a server-based engine that is optimized for performing the core functional and computational duties within gene expression module 200. Analysis engine 230 communicates and links between the explorer interface 220 and the data warehouse 210 while providing the primary power for all complex analysis tasks.

The improvements disclosed herein are intended for incorporation and interaction with the gene expression module 200 and do not require the inclusion of connector module 300 to achieve the desired function. Accordingly, with reference to FIG. 1, the connector module 300 and the proprietary customer data 402 can be omitted, with a user interface (e.g., network workstation 400) providing direct access to gene expression module 200 for querying and viewing of query results. Nonetheless, the following provides a brief description of connector module 300 and its operation, which provides the advantage of permitting addition of proprietary customer data 402 to the existing data in the data warehouse 210 for query and analysis based on the combined data record. Thus, the improved method and systems disclosed herein can be utilized for management and analysis of data that is pre-existing in the data warehouse 210, or data that is the combination of imported customer data and pre-existing data when connector module 300 is included.

Connector module 300 permits a user to load more than one source of gene expression, and sample information in the data warehouse 210 of gene expression module 200. In particular, connector module 300 permits a system user to load the user's expression data and sample data from external files into the data warehouse for comparison or combination with a pre-existing, internally-stored set of data, i.e., the data already existing in data warehouse 210. To facilitate distinction between the different data sources, the latter data may be referred to as the "pre-existing data" while the user's data will be referred to as "customer data." Connector module 300 provides an interactive interface to manually add and edit sample data through a sample data manager, which provides validation and migration of sample data from external files into the system. An XML sample migration template facilitates preparation of sample data for migration. After the expression and sample data have been loaded via the connector module 300, the user can view, query and analyze the user's own data together with the pre-existing data.

The connector architecture preferably is object-oriented so components can be developed and modified individually. Wherever possible, schema-dependent rules and logic are stored outside the code so that schema changes can be readily made without affecting the code.

The connector database and server components preferably run on hardware from Sun Microsystems, Inc. of Palo Alto, Calif. on the Solaris™ 8 Operating Environment also from Sun Microsystems. The database is preferably Oracle Server 8.1.7.3. Other software includes Visibroker® C++3.3.2 from Borland Software Corporation of Scotts Valley, Calif., Java 2 SDK version 1.3.1.03 available on the WWW from Sun Microsystems, Apache HTTP server 1.3.12 and Xerces-c 1.7.0 XML parser both from Apache Software Foundation, Expat 1.95.2 XML parser library available via the Internet from SourceForge, and Perl 5.6.0 and 5.6.1. For any of the identified software, a later version may be used as well. Supporting documentation for the hardware and each of the listed software programs is incorporated herein by reference for purposes of this disclosure. For more information on the exemplary system architecture described above, the reader is referred to commonly-assigned U.S. application Ser. No. 10/090,144, and PCT Application Serial No. US02/19877, which have previously been incorporated herein by reference.

Figure 3:
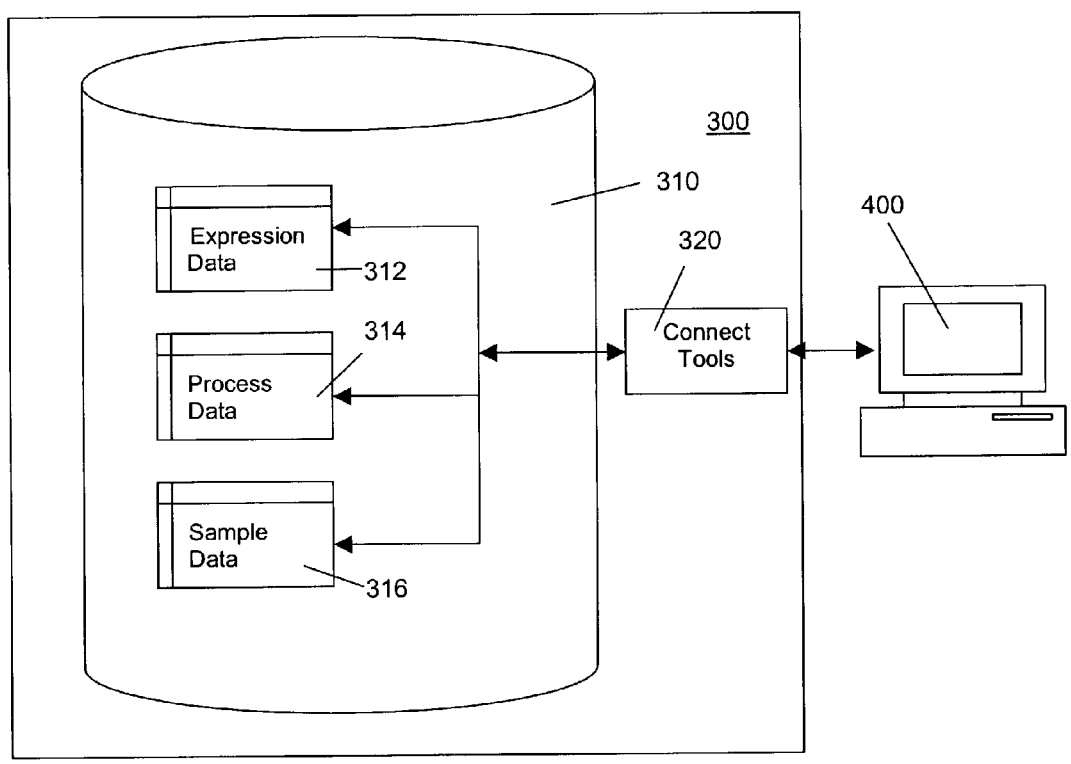
FIG. 3 is a block diagram of the connector module of the platform.
Figure 4:
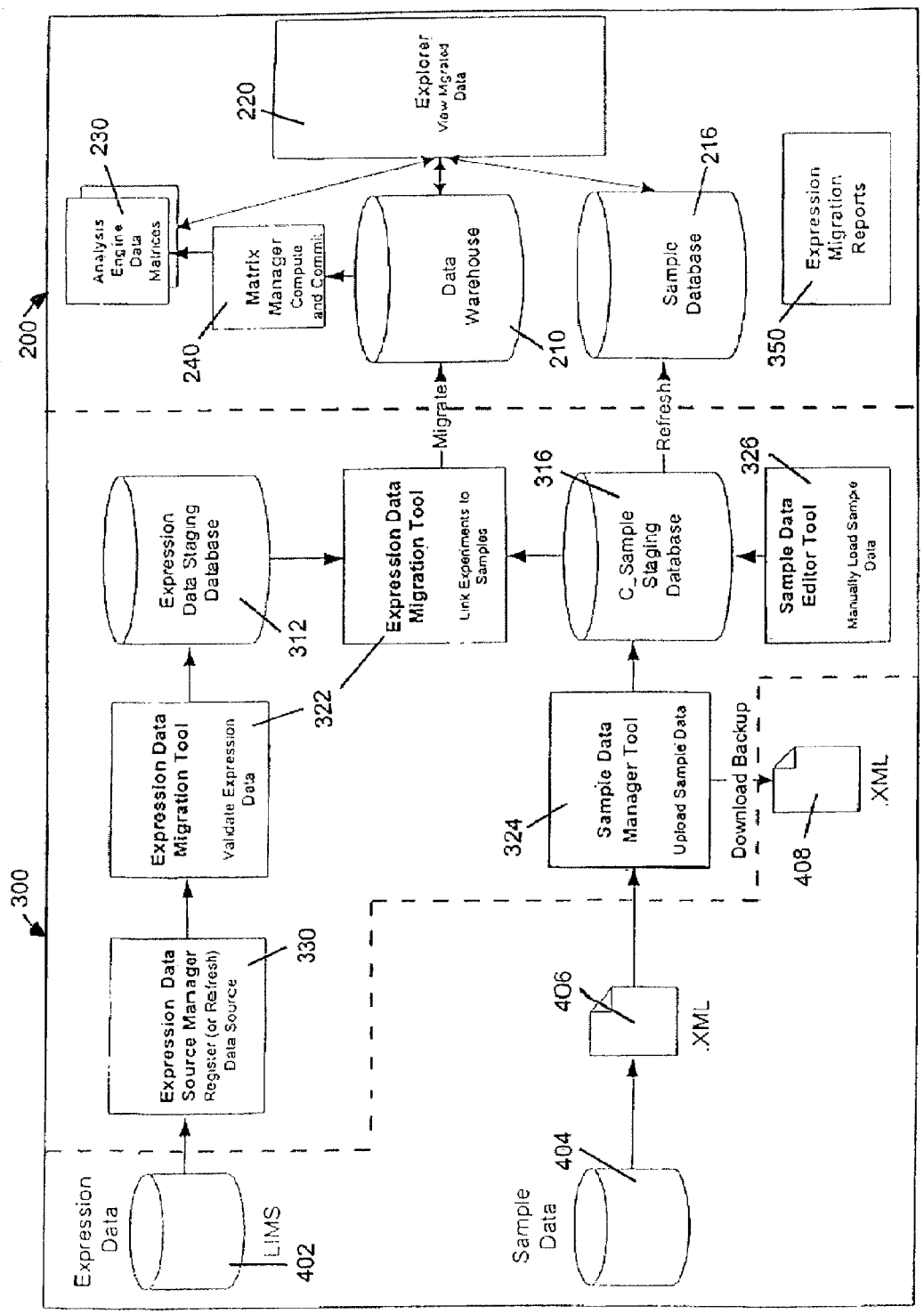
FIG. 4 is a more detailed block diagram showing data flow through the connector module.

Referring to FIG. 3, the basic architecture of connector module 300 is illustrated and includes connector data staging platform 310 which is partitioned into three different databases. Connector expression data manager 312 stages user-selected expression data from GATC/AADM external sources for migration into data warehouse 210. Expression data manager 322, shown in FIG. 4, provides validation, transformation and migration of expression data into the data warehouse 210. Data within expression staging database 312 is transient. ID values are offset to eliminate clashes between existing data and customer data.

Connector sample database 316 stages customer samples loaded from an XML file prior to loading into sample database 216 of data warehouse 210. The user's sample data is preferably drawn from a pre-defined sample template in XML format. The connector module provides a function allowing the user to enter or modify the user sample data using the sample data editor. Database 316 also serves as the underlying database for a sample data editor which allows the user to enter new sample data or to revise customer sample data entered through XML file loading.

Database 316 is persistent and thus not transient. However, each sample template data loading from an XML file will overwrite existing sample data in the sample staging database. Therefore, the sample staging database contents should be backed up before each new XML data loading. Therefore, a user can always recover the sample staging database should he/she make a mistake. Certain data are classified static-dynamic. This data is moved into the data warehouse only if it does not already exist in the warehouse. If it does exist, the reference to it in the customer data is synchronized with what already exists in the warehouse. Such data includes TARGET_TYPE, and PROTOCOL_TEMPLATE.

Connector process database 314 stores detailed references to the customer's expression and sample data, configuration information and event logs for all processes performed within the connector module 300. Data stored in this database is persistent. However, deleting source or unmigrating experiments will cause the corresponding data to be removed from the connector process database 314. References to static data are synchronized in customer data to the gene expression module 200 so that both use the same ID value for a given name.

The user interface 400 communicates with the connector module 300 to provide the user with the ability to perform expression and sample data loading. The connector module 300 also communicates proper status information, messages and viewing functions to the user via the user interface 400.

Operations by connector module 300 only affect operation of the gene expression module 200 when data is migrated into the data warehouse 210 and the analysis engine is synchronized. This is due to the fact that the connector processes are usually relatively long-running. When this occurs, all users who are connected with the gene expression module 200 will be required to restart their application.

FIG. 4 provides a more detailed diagram of the functions performed by connector module 300, including a number of connector tool functions. Gene expression data from data source 402 is loaded through a user interface, not shown, which may include a network workstation or may be a separate station in a laboratory system having an Affymetrix® LIMS Oracle database. If the user's expression data are in other compatible types of systems or flat files, then the data is preferably downloaded, processed and uploaded into a LIMS Oracle database. The gene expression data enters module 300 through the expression data source manager 330 which acts to register data source 402 and extract a list of experiments from this data source. Expression data source manager 330 includes the ability to refresh the experiment list of a registered expression data source 402. Expression data migration tool 322 is used to validate expression data, create links between experiments and samples, queue data for migration and migrate the expression data into the data warehouse 210. Expression data staging database 312 acts as a staging area for expression data during operation of data migration tool 322.

Sample data 404 is preferably entered into a pre-defined sample template 406 in XML format, and then uploaded into the sample staging database 316 using the sample data manager tool 324. This tool 324 is used to upload, refresh and backup sample data. As described above, because each sample template data loading from an XML file overwrites existing sample data in the sample staging database 316, the existing sample database content is backed up in an XML data file 408. If necessary, the user can access overwritten sample data via the XML data file 408. All tables representing customer sample data are truncated during XML file upload. Tables for controlled vocabularies and ID mapping information are not truncated.

Sample data manager tool 324 uploads the XML data file into the sample staging database 316 by parsing with a Perl XML parser. The XML parser also verifies the correctness of the sample data file. If the XML data file passes the syntax checking and validation, then Oracle Structured Query Language ("SQL") Loader control and data files will be generated for bulk loading customer sample data into the sample staging database 316.

Customer sample data in the sample staging database 316 is downloaded into the sample template XML format using a Perl script which takes a control file to download customer sample data in the database into an output XML file. All customer sample data in sample staging database 316 is preserved in the XML output file. However, the XML output file may not be identical to the original sample template XML file because some attributes with null values can be assigned with default values in database 316 by the loader.

Sample staging database 316 serves as a staging area for storing sample data prior to migration and for refreshing sample data in the gene expression sample database 216. Links between sample data and expression data are staged in the expression data staging database 312. Note that although sample database 216 is preferably encompassed within data warehouse 210, it been shown as having distinct structure from the data warehouse to facilitate illustration of the different handling of the migrating sample data. Sample data editor tool 326 is used to manually enter sample data, and to edit sample data that may have originally been uploaded as an XML file.

In operation of connector module 300, there are 6 major steps to be performed in loading of customer expression data:

1. Register and initialize or refresh an expression data source: This function is handled in expression data source manager 330. A user first registers an expression data source Oracle database, e.g., database 402, by entering the Oracle database information, such as TNS name, host name, port number and/or SID, and user logon information, such as user name and password. All experiments in this Oracle database will be recorded in a master experiment list. When new experiments have been added to a registered expression data source, a user can refresh the master experiment list for this data source.

2. Extract and validate selected experiments into the staging database: This operation is performed by expression data migration tool 322. A user selects a list of experiments from a registered expression data source. All experiments in the same batch come from the same expression data source. However, a user may also be allowed to select experiments from different expression data sources in different batches. All expression data sources should be registered by expression data source manager 330 first. All selected experiments are preferably validated by expression data migration tool 322 to determine whether the data are "complete." All validated experiments are staged in the expression data staging database 312 for further operations. Proper ID value transformation is performed before data are loaded into the expression data staging database 312 to ensure that the user expression data and the standardized expression data are using different ID spaces.

3. Upload sample data and link experiments with sample data: Sample data 404 is preferably uploaded via sample XML file 406 via the sample data manager tool 324. A portion of an exemplary sample XML file is provided in FIG. 5. Alternatively, the sample data can be manually entered via sample data editor tool 326, for example, if a relatively small amount of data is to be loaded, or the data are not in a database but are taken directly from lab notebooks. Once uploaded, the sample data is staged in sample data staging database 316 until it is linked with the experiments by expression data migration tool 322. Each experiment is preferably associated with only one sample, however, multiple experiments may be linked to the same sample.

4. Migrate the data into the data warehouse: This function is carried out by expression data migration tool 322 after the sample-experiment links are completed. Only validated and linked to sample experiments can be migrated into the data warehouse. The migrated experiment data will also be loaded to the analysis engine 230 in gene expression module 200. An "un-migrate" operation is provided to allow a user to remove migrated experiments from the data warehouse 210 and the analysis engine 230.

Different migration strategies may be used depending on the size of the databases. For migration of sample data into sample database 216, the size of the connect sample database and the sample database in gene expression module 200 is relatively small. Therefore, a full refresh is performed for each migration as follows: mapping between the connector sample and the pre-existing sample objects is done for all connector sample objects. Next, data is retrieved from the connector sample database 316 based on a metadata control file and SQL loader files are generated for loading into sample database 216. All customer data in sample database 216 are removed using SQL delete statements. The customer data in sample database 216 is offset with predetermined ID ranges. The customer sample data is loaded into sample database 216 using Oracle SQL loader.

Because gene expression data and process data databases may both be relatively large, no full refresh is performed. Only user validated and linked experiments are migrated into the data warehouse 210.

5. Compute and commit migrated data: This operation takes place in matrix manager 240 of gene expression module 200. In order for the migrated data to be available to the explorer interface 220, the analysis engine 230 must be refreshed using the matrix manager 240. Matrix manager 240 refreshes the expression data in the analysis engine 230 and copies the expression data that have been computed into the analysis engine 230.

6. Viewing migrated data in the explorer interface 220: At the completion of the migration process, migrated data are available within the explorer interface 220. At this point, migrated data can be queried, saved and analyzed just like other pre-existing data in the data warehouse 210 by way of the user interface and selection of the desired option.

Additional information about the connector process is available through expression migration reports 350. This function is primarily administrative, for tracking the status of migration operations and includes filtering options for selecting specific information such as the type of operations performed, types of samples migrated, donors, study groups, etc. The administrator can also check on the system function and status, including Java RMI server activity, RTE information, e.g., refreshes and updates, database synchronization, etc.

Figure 6:
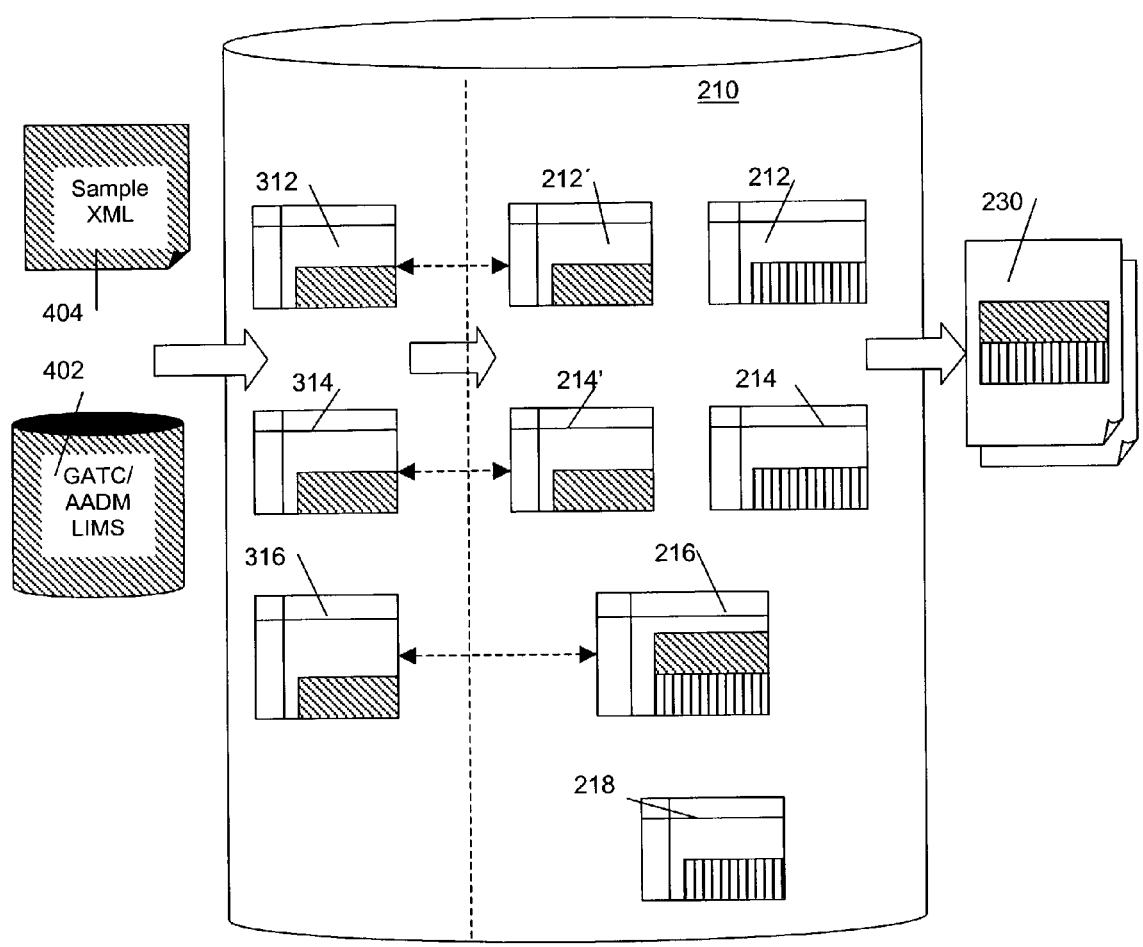
FIG. 6 is a block diagram showing customer data migration into and storage in the data warehouse.

After migration of data into data warehouse 210, the pre-existing expression data and customer expression data reside in different database partitions. As illustrated in FIG. 6, customer data is designated by angled fill lines while pre-existing data is designated by vertical fill lines. Customer gene expression data 402 and sample data 404 migrate into the data warehouse 210 through staging databases 312 and 316 in connector module 300. Customer process data is loaded through process staging database 314. After migration, the customer's gene expression data is maintained in data warehouse 210 as a separate expression data file 212' from pre-existing expression data file 212, even though, for purposes of analysis, the analysis engine 230 will look to both data to satisfy a search query. Accordingly, the data matrix within analysis engine 230 is illustrated as containing data corresponding to a combination of both customer and pre-existing data.

By maintaining a partition between the pre-existing data and the customer data within data warehouse 210, the pre-existing data can be updated or modified while the customer's expression data remains intact. Also, the customer's proprietary data is not merged into the broader database in a way that might be accessible to other customers.

In a similar manner, the customer process data from process staging database 314 is maintained in a separate database 214' from the pre-existing process database 214.

Customer sample data from staging database 316 is combined with pre-existing sample data in database 216. No customer data is combined with gene index 218; all of the information contained in this database is pre-existing relative to the customer's data.

The data matrices within analysis engine 230 are managed by the matrix manager 240, shown in FIG. 4. Matrix manager 240 merges data by creating a union of corresponding matrices from two sets of data. The merging is performed when customer data is migrated into the data warehouse, to combine pre-existing data with the customer data. The merge also occurs when the pre-existing data is updated, for example by adding new data. Any of the four databases within data warehouse 210 can be updated. Matrix manager 240 takes into consideration the sample IDs that have been assigned to customer data and the old pre-existing data so that when new data is added to the pre-existing database, the new data will take precedence over the customer data and the old pre-existing data. For example, if there are samples with the same sample IDs, the expression and call values in the unioned matrices will be from the sample with higher precedence.

Referring briefly to FIG. 1, access to functions of the platform 100 is initiated using a launcher which is downloaded on each network workstation 400 on which a user wishes to utilize the platform's capabilities. The platform 100 is intended to be accessed from and used by multiple workstations.

The network workstation is preferably a 500 MHz Pentium III or faster processor running Windows NT 4.0 or later with at least 50 MB of free hard drive space, 256 MB of RAM and virtual memory set to 256 MB; a color monitor with at least 1024×864 pixels and 256 colors, 1152×864 pixels and 65536 colors are recommended; Netscape Navigator version 4.7 or Internet Explorer version 5.0 or later; a workspace account; and a Java Run time Environment ("JRE"), preferably version 1.3.0 or later.

In addition, other commercial software packages are preferably available to augment the platform 100, including Spotfire® Pro version 4.0 or later and Spotfire® Array Explorer, both marketed by Spotfire Corporation of Cambridge, Mass. for visual examination of gene data exploration results; or Microsoft® Excel 2000®; Eisen Cluster Tool; GeneSpring® from Silicon Genetics of San Carlos, Calif.; S-plus®, from Mathsoft Corporation of Seattle, Wash.; or Partek® Pro 2000, etc. for analysis with statistical tools.

Those skilled in the art should appreciate that the systems and methods according to the invention may be implemented over a network environment. The network may be any one of a number of conventional network systems, including a local area network ("LAN"), a wide area network ("WAN"), or the Internet, as is known in the art, e.g., using Ethernet, IBM Token Ring, or the like. In addition, the present invention may also use data security systems, such as firewalls and/or encryption.

To install at least some of the software associated with the platform 100, a user points his/her Web browser to the universal resource locator ("URL") providing the home page of where the software can be downloaded. The user can then select the download option, which opens the download and installation page of the software. Among other things, this page provides instructions for completing the two steps for installing the software: installing the Java Run time Environment and installing the launcher for the software.

Over time, a user of the platform 100 will develop a large number of sample sets, gene sets, and analysis results. The platform 100 preferably incorporates a workspace which serves as a centralized repository for these data objects, organized into user-defined project folders. Access to the workspace is preferably controlled through user names, user group affiliations, and passwords. User-defined data objects are by default private to the user; however, during the save process, the user preferably has the option of making data objects accessible to other users.

The relational database preferably utilizes a three-layer archiving system. The three layers are: (1) an on-line network disk file system; (2) near-line storage; and (3) off-line DLT tape backups. The on-line network disk file system is based on a network disk system, such as Network Appliance F720. The network file system is also visible to the NT network. The disk space is organized into two partitions: one for archiving and one for building data distributions. A complete set of information for each sample in a file system accessible from both UNIX and Windows® is maintained. The information is organized by genomics identification number and can be further broken down by experiment name. By storing the information in this directory structure, it is easier to build distribution sets based on filtering requirements. The near-line storage is based on an HP Superstore magneto-optical jukebox and serves as the backup device of all data files generated by production and is also the backup of the on-line archive.

Off-line DLT tape backups are used to backup the pre-staging directories, the database servers and the on-line archive.

The platform 100 performs certain functions that are disclosed in more detail in the related applications, which have been incorporated herein by reference. For example, the detailed operation of the gene expression analysis engine, including the analysis algorithms, is disclosed in application Ser. Nos. 09/862,424, 09/797,803, 10/096,645, Ser. No. 10/090,144, and PCT application Serial No. US02/19877. The detailed function of the connector module is disclosed in application Ser. No. 10/096,645. The platform 100 provides integration, management and analysis of large amounts of gene expression data from different sources. It provides extensive capabilities for capturing and analyzing associated clinical and experimental information. The platform 100 further provides curated public and proprietary information about the genes represented on the microarrays, adding instantaneous biological context to the expression data. Gene information includes data obtained from a large number of public databases. The connector capability of the platform 100 enable the combination of multiple data sources, giving researchers the ability to analyze their own data in light of an extensive database.

Figure 7:
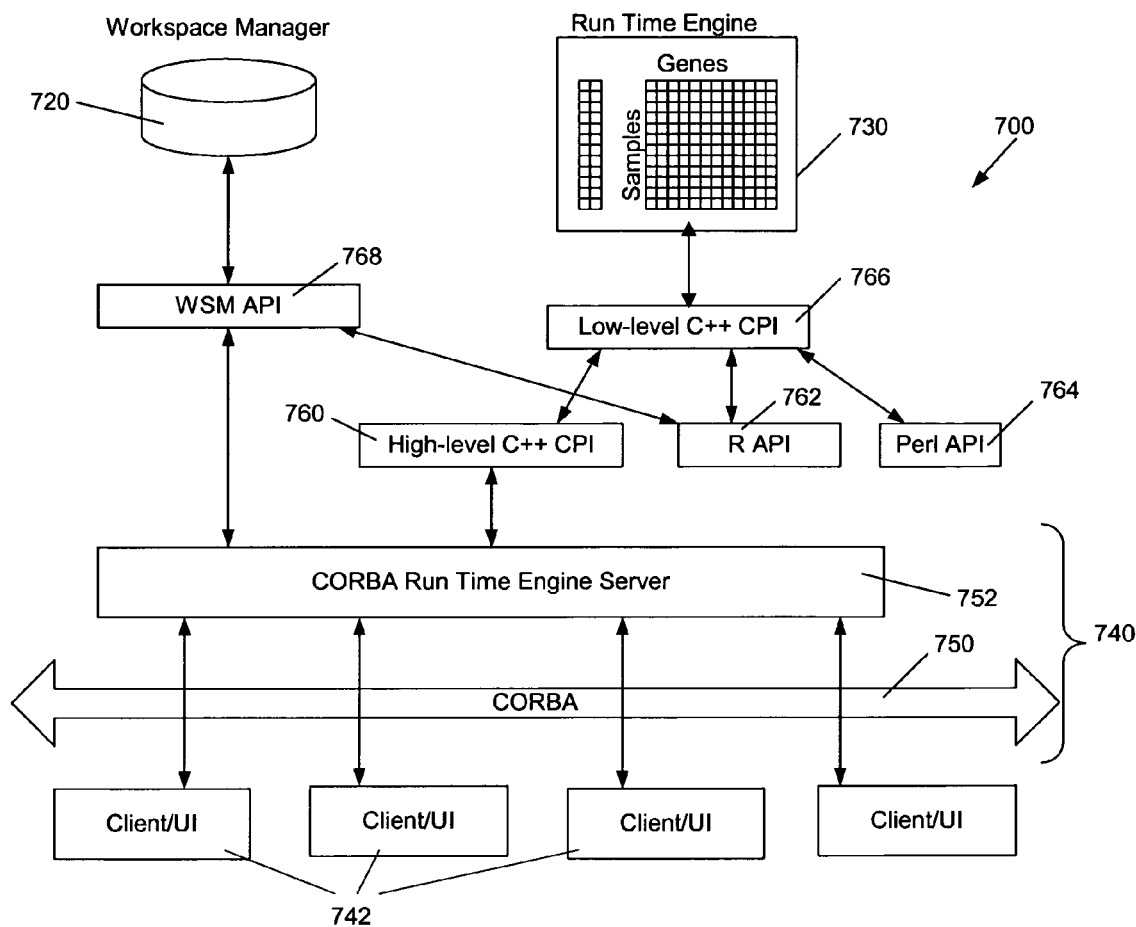
FIG. 7 is top level view of a platform according to a second embodiment of the invention.

A platform 700 according to a second embodiment of the invention will now be described with reference to FIG. 7. FIG. 7 shows a partial diagram of the platform 700, with remaining portions of the platform 700 being similar to the platform 100 shown in FIG. 1. In general, the platform 700 provides for a faster and more efficient analytical engine 730, also referred to as a Run Time Engine ("RTE") 730, in which data is downloaded in an efficient file format that serves as the basis for analysis computations in the gene expression data warehouse. The platform 700 includes scripts and binaries to download data into memory mapped files. Further, the platform includes tools for cloning the memory mapped files to aid in customizing deployment data. The computations supported by the RTE 730 include, but are not limited to, the following methods: gene signature, gene signature differential, fold change, e-Northern, and contrast analysis. Programming access to the RTE 730 may be through one of the following APIs. These APIs (application programming interfaces), which are on top of a high-level C++ API 766, include, but are not limited to, a Perl API 764, a CORBA API 740, and an R API 762. The CORBA API 740 is implemented through a CORBA Run Time Engine Server 752 which is used to communicate with the workspace through a high-level C++ API 760. The CORBA API 740, Perl API 764, and R API 762 are at the same level, built on top of the high level C++ API 760.

The low-level C++ API 766 reflects an underlying implementation and memory model of the RTE 730. The low-level C++ API 766 provides access to individual data stored in the RTE 730 through functions and methods. Tools using this API could include Unix command-line tools for loading and dumping data, and the higher level API libraries described below.

The high-level C++ API 760 uses C++ classes and methods to provide a conceptual view of the RTE 730. The high-level C++ API 760 includes support for various higher-level concepts, such as Gene Sets and Sample Sets, that are used by the U1742 (user interface) and analysis tools. This API 760 is used for developing the servers accessed by the UI 742 and the CORBA API 740. The high-level C++ API 760 may be provided to outside developers wishing to access the RTE 730 directly in C++, without using CORBA 740.

The CORBA API 740 is based on the high-level C++ API 760, with additional classes and methods necessary for performing the various analysis functions required by the UI 742. The CORBA API 740 is used by the UI 742 and other client programs for accessing the RTE 730. This API 740 is also the preferred API for outside developers.

The Perl API, using PDL (Perl Data Language) module 764 allows simple access to normalized data stored in the RTE 730. This API 764 may be used for writing export tools and web interfaces, such as the case of the current version of ToxExpress®. The Perl API 764 is built directly on top of the low-level C++ API 766.

The R API 762 uses R, a freely available clone of the statistical package S-plus under the General Public License ("GPL"). R has "hooks" for programming in C/C++. As a scripting language for the RTE 730, the R API 762 is preferred over the Perl API 764 because its unit of manipulation includes vectors and matrices, which are more efficient data structures than are individual Perl objects. The R API 762 allows for access to data stored in RTE 730, including all normalizations, an Oracle database connection, as well as to workspace data via the WSM API 768. The R API 762 is ideal for the purpose of quickly writing custom analysis methods and may be useful for setting up "web reports" that include statistical analysis methods.

In a preferred embodiment of the present invention, the RTE 730 is made faster and more efficient by providing code at a level closer to the machine level. Instead of relying primarily on object-oriented constructs and using function calls, the platform 700 uses more direct accessing to the memory data structures in the RTE 730.

With reference to FIG. 7, the platform 700 includes new workspace file system ("WFS") which is constructed on top of a file system, preferably the Unix File System. In comparison to the platform 100 in which the data warehouse 210 is preferably Oracle-based, a workspace manager 720 is more efficient in performing its required operations, as will become more apparent from the description below. The workspace manager 720 and overall WFS are more accessible and flexible than the Oracle-based data warehouse 210 because standard Unix File System tools, such as cp, mv, and perl, may be used to manipulate the contents of the workspace directly instead of interacting through SQL formatted commands. The WFS and workspace manager 720 allow for smoother evolution of the workspace data and facilitate the merging of multiple workspaces with little effort. Users from other workspaces may be incorporated into a workspace. Custom data may be generated to populate the workspace.

The new workspace allows data objects to be split between an XML descriptor and its binary attachments. Instead of using tag-value property settings, XML is being used which allows for more complex structures. With XML, object names are no longer internal data content, but part of the file system name. The XML descriptor allows for fast access of descriptive information, such as ownership, permissions, description, and gene chip set, without having to access the bulk of the actual data. The binary attachments, stored in Binary Large Object ("BLOB") files, can be any application-specific binary format. The WFS and workspace manager 720 allow for fast machine in put of a binary image for bulk data without having to parse ASCII. Interpretation of the BLOB bytes is dependent upon descriptor information in the XML files and a given application program. An XML descriptor may have multiple binary attachments.

An example of an XML descriptor stored in the workspace is as follows:

```
<DataObject>
  <wfsNode>
    <_type>d</_type>
    <_ownedBy>szeto </_ownedBy>
    <_groupPerms>opm:0    gxdb:1    admin:0</_groupPerms>
    <_worldPerm>0</_worldPern>
    <_createDate>12/30/2000 20:20:35</_createDate>
    <_createClockTime>978236435</_createClockTime>
    <_modDate>12/31/2000 10:20:01</_modDate>
  </wfsNode>
  <SampleSet>
    <geneChipSet>1</geneChipSet>
    dataStore type="blob">samples. 0.123</dataStore>
  </SampleSet>
<DataObject>
```

The attribute type="blob" indicates a binary attachment. The BLOB file samples.0.123 resides in a special BLOB directory. Other XML elements in this example contain values from C++ data structures.

Another example of an XML descriptor stored in the workspace is as follows:

```
<?xml version='1.0'?>
<SampleSet>
<geneChipSet>1</geneChipSet>
<description>Demo Sample Set </description>
<dataStore>blob123</dataStore>
</SampleSet>
```

As with the first example, blob 123 is an binary attachment tag to the BLOB inserted in the blobs argument. The "blob 123" is a "temporary" tag for the sake of correlating the XML descriptor value with the binary value entry. The actual workspace storage translates the BLOB to a unique name. The temporary blob name should be unique within the XML entry so as not be confounded with another XML value.

Struct iWfsBlob
tag ="blob123"
type ="some app type name"
bytes =<add your bytes here>

Interpretation of the bytes are application specific through the XML descriptor. In this case/SampleSet/dataStore is an application type, and the bytes are interpreted accordingly.

Figure 8:
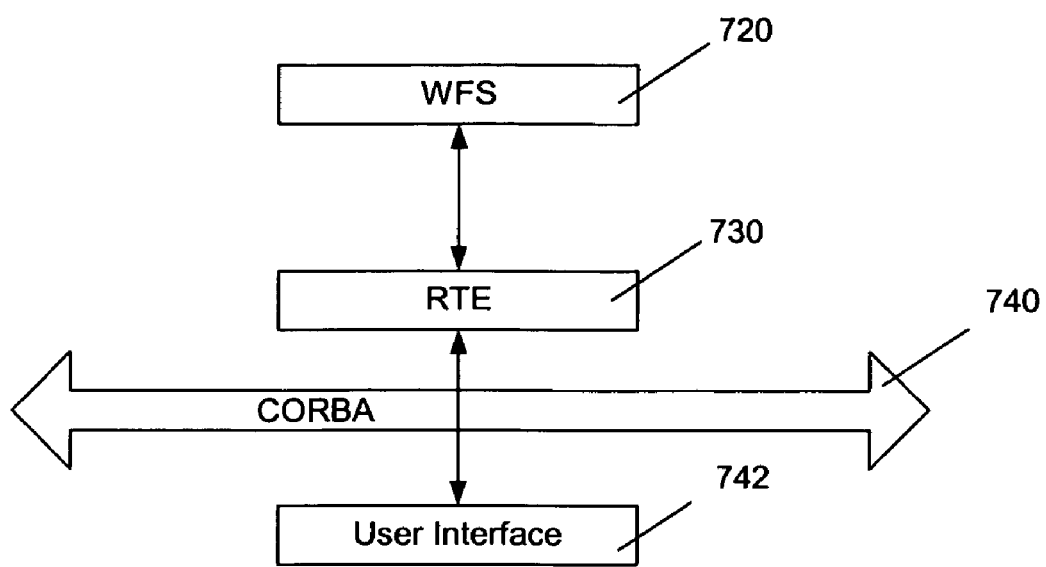
FIG. 8 is a diagram representing the relationship between a workspace manager and a Run Time Engine (RTE) within the platform of FIG. 7.

As represented in FIG. 8, the workspace manager 720 and overall WFS is hidden behind the RTE 730. When the RTE 730 is started, a corresponding workspace manager 720 is also started. The workspace manager 720 allows for raw binary storage of data and the RTE 730 does the application specific interpretation of the bytes that makes sense in its context. Users may access the workspace manager 720 through the lower level C++ API 766. Client applications either have the opportunity to deal with storage at the binary level, or to use the RTE API to save and load RTE data objects. For manipulating folders, objects in folders, and setting permissions, one needs to use the WFS API 768. For objects involving BLOB's, such as SampleSets and GeneSets, the RTE API 766 is recommended. For all others, one may use either API.

A number of tools may be used to work with the contents in the workspace. For example, wfsterp is an interpreter/shell which allows for manipulation of users, groups, folders, permissions, and data objects in the workspace. A wfsPerl tool provides a Perl API for manipulating contents of the workspace. The wfsPerl tool is useful for migration tools, gene scripts to load public Gene Sets, and other custom applications. A wfsServer tool provides a CORBA interface and server implementation to access the workspace and is used mainly by the Java UI's, or architectures whereby the client does not reside on the same host as the workspace storage data. An xmltrans tool enables custom parser using a Simple XML Translator ("SAX") that parses an XML file into a tree data structure, and prints the tree in pretty format, i.e., pretty prints the tree. A longTrans tool is a custom translator for translator binary files that are an array of longs. The longTrans also performs "gene interpretation" to pretty print gene ID's in element pairs. The Unix tool "od" can be used for the same purpose, but it is not as user readable. In addition to these exemplary non-limiting tools, other standard Unix File System tools may be used, such as mv, cp, mkdir, od, and Perl. Perl may be used to manipulate binary files, WFS blobs, with the pack( ) and unpack ( ) functions.

As discussed above, the RTE 730 provides rapid access to certain core data and derived data from the data warehouse 210. The RTE 730 provides more rapid access to these data than could be achieved using a Relational Database Management System ("RDMBS") directly, such as the relational database discussed above with reference to the platform 100, and thus improves the performance of various analysis operations used by the UI 742 and other client programs. The data stored in the RTE 730 comes ultimately from the RDBMS, by way of daily updates performed in off-hours.

The following data are represented in the RTE 730:
1. Absent/Present calls for each sample/gene pair. Multiple sets of A/P calls are represented, for example those generated using different versions of the Affymetrix® LIMS.
2. Intensities or expression values (Av. Diff. Values) for each sample for each sample/gene pair. Several forms of normalizations are supported.
3. Chips available for each sample. The chips available for any sample are a subset of the appropriate chips for the species of the sample.

The high-level C++ API 760 implements many types, classes and methods, including data types, e.g., samples, genes and gene chips, combinations thereof and analysis results, workspace manager objects, interface classes, etc.

The class "Samples" represents the tissue samples in the data warehouse 210. Each sample may be associate with experiments using some sub-set of the associated gene chips. The class "Gene" represents a probe-set on an Affymetrix gene chip. Each gene is represented by a chip ID and a probe ID. There are different groups of gene chips, such as the Affymetrix 42K chip set and the 60K chip set. The RTE interface allows users to set any of these chip sets for further operations. Once a gene chip set is selected, all operations are based on the data from the selected gene chip set. Sets of chip IDs are associated with each Sample in the RTE 730.

The class WMObject is used to represent the common properties of any object that may be stored in the workspace manager 720, such as sample sets, gene sets, gene signatures, etc. Each object of class WMObject may be either permanent or transient. A permanent WMObject is one that has been saved in the workspace manager 720 and assigned a workspace manager identity. A transient WMObject is one that has not yet been saved, and so exists only in the RTE server. In general, any WMObjects that are submitted to the RTE 730 by the UI 742 for manipulation must first be saved in the workspace manager 720 and will, therefore, be permanent. However, certain RTE operations may generate new objects, such as gene signatures or their component gene sets, which will initially be transient. These transient objects may be made permanent by saving in the workspace manager 720.

The classes SampleSet and GeneSet are used to represent ordered sets of Sample IDs and Gene IDs, respectively. These classes consist of ordered elements that are repetition free sequences of Samples or Genes. Both SampleSet and GeneSet inherit from the WMObject, so they may be either permanent or transient. Any GeneSets or SampleSets submitted by the UI 742 to the RTE 730 for manipulation must first be saved in the workspace manager 720 and will, therefore, be permanent. The UI 742 sends Workspace Manager IDs to the RTE server rather than passing the contents of a GeneSet or SampleSet. Certain RTE operations may generate new GeneSets and SampleSets, which will initially be transient. For example, a gene signature operation would generate two transient GeneSets, describing the present and absent genes.

The class SampleSlice is used to represent a restriction of the RTE matrices of intensities and A/P calls for a given SampleSet. The class supports methods that, for a particular Gene ID return an array of A/P calls, p-values or intensities indexed over the items of the SampleSet. It also supports methods that provide summary data, such as the total counts of Present, Absent, Marginal or Unknown calls for each Gene ID on a specified chip. Implementation of the SampleSlice class functions as an interface to the data stored in the RTE 730 rather than storing copies of the data.

When retrieving A/P/M/U call values and associated data, a parameter of enumerated type PAType is used to specify the kind of analysi that was used to generate the A/P/M/U call. When retrieving intensities, a parameter of enumerated type IntensityType is used to specify the kind of intensity value, e.g., type of normalization, to be retrieved.

The class SampleSlice supports methods used to calculate gene signatures and gene signature graphs. Separate methods are used for generating each of the two gene signature curves, which can be display by the UI 742 while the gene signature is being computed. Preferably, two methods are used for computing the present genes curve and the absent genes curve because the absent genes set is usually much larger than the present genes set.

The class GeneSignature represents the result of the gene signature analysis. A gene signature is represented by two GeneSets: the present genes and the absent genes. In addition, a GeneSignature provides access to the SampleSet on which the GeneSignature is based, the thresholds used, and various summary data. The summary data includes the total counts of present and absent genes; for each gene in the present GeneSet, the number of samples for which the gene is present and number for which it is unknown; and for every gene in the absent GeneSet, the number of samples for which the gene is absent or marginal, and the number of which the expression is unknown.

The class GeneSigDiffer represents a gene signature differential analysis for two conceptual gene signatures. The main components of a GeneSigDiffer are four GeneSets: the set of genes present in both GeneSignatures; the gene present in the first and absent in the second; the genes absent in the first and present in the second; and the genes absent in both. A GeneSigDiffer also provides method to return a summary of results, including the size of the four GeneSets. SampleSet inputs may be used to implement a more efficient algorithm that quickly calculates the differentials without fully calculating the gene signatures themselves.

The class GeneSlice is used to represent a restriction of the RTE matrices of intensities and A/P calls for a given GeneSet. The class supports methods that, for a particular Sample IS, return an array of A/P calls, and intensities indexed over the items of the GeneSet. This class also supports methods that provide summary data, such as total counts of Present, Absent, Marginal or Unknown calls for genes in the GeneSet for a specific Sample ID. In addition, GeneSlide supports methods to create E-Northern analysis of a given sample set. The implementation of the GeneSlice class functions as an interface to the data stored in the RTE 730 rather than storing copies of the data.

The class ENorthern performs electronic Northern analysis of a vector of SampleSets for genes in a given GeneSet. For each gene in the GeneSet, an E-Northern analysis will provide a record consisting of the number of Present calls and the number of Absent calls in the SampleSet for the gene, and also the ranks of the lower percentile, upper percentile and median samples for the gene.

The class FoldChange represents a fold change analysis between two sample sets, for a given confidence level. FoldChange supports a method for obtaining the results of a fold change analysis within a range of values, a method to recalculate a fold change analysis for a different confidence level, and method to obtain summary data on the current fold change analysis.

The RunTimeEngine class provides an interface to the data stored in the RTE 730. It provides access to the individual expression data and P/A/M/U calls for any GeneId/SampleID pair. It preferably supports methods that return the set of chips for which data is available for a particular sample or for all samples in a SampleSet. In addition, the RunTimeEngine class supports methods to create SampleSlice, GeneSlice and FoldChange analysis objects.

The main interface class of the Run Time Engine server is called iRunTimeEngine. This class acts as the main entry point to the server. It supports methods equivalent to those of the C++ class RunTimeEngine. The RTE servers are run in unshared mode, i.e., one RTE server process is paired with each instance of a UI client. The memory mapped file pages representing the RTE data are shared in memory.

The foregoing description of the preferred embodiments of the invention has been presented only for the purpose of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated.

What is claimed is:

1. A platform comprising a processor executing a program for analyzing gene expression data, wherein the platform comprising:
   a data warehouse comprising a plurality of databases for storing gene expression data, sample data that corresponds to the gene expression data, and gene index data that identifies the gene expression data, wherein the plurality of databases are integrated into a relational database having a relational database management system for managing data flow to and from the data warehouse;
   a run time engine receiving gene expression data from the data warehouse by means of the relational database management system; storing the received gene expression data in the form of core and derived gene expression data arranged in a matrix of absent/present calls and intensities or expression values for each sample/gene pair in memory mapped files in a workspace file system; wherein the run time engine comprising a plurality of analysis tools that accesses and analyzes the core and derived gene expression data in the memory mapped files in the workspace file system using a low level code, without directly accessing the relational database management system;
   a matrix manager disposed between the data warehouse and the run time engine copying and refreshing the core and derived data into the matrix by creating a union of matrices from two sets of data;
   a first application programming interface for accessing gene expression data, the first interface comprising a low-level interface providing direct access to individual core and derived gene expression data in the memory mapped files;
   a user interface to the plurality of analysis tools for entry of analysis queries and output of query responses;
   a second application programming interface coupled between the user interface and the first application programming interface transferring analysis queries to the first application programming interface, wherein the second application programming interface comprises a high-level interface to the run time engine; and
   a display outputting one or more gene signatures, gene signature graphs, fold change, and ENortherns generated from the analysis of core and derived gene expression data from the run time engine.

2. The platform as set forth in claim 1, wherein the first application programming interface comprises a low-level C++ interface.

3. The platform as set forth in claim 1, wherein the second application programming interface comprises a high-level C++ interface.

4. The platform as set forth in claim 1, further comprising a third application programming interface, the third application programming interface coupled between the user interface and the first application programming interface, the third application programming interface transferring requests for the gene expression data initiated through the user interface to the first application programming interface.

5. The platform as set forth in claim 4, wherein the third application programming interface comprises a Perl application programming interface.

6. The platform as set forth in claim 4, wherein the third application programming interface comprises an R application programming interface.

7. The platform as set forth in claim 1, wherein the user interface comprises a CORBA user interface and wherein the platform further comprises a CORBA run time engine server positioned between the CORBA user interface and the second application programming interface.

8. The platform as set forth in claim 1, wherein the first application programming interface is adapted for loading gene expression data into the data warehouse.

9. The platform as set forth in claim 1, further comprising a workspace manager file system located between the first application programming interface and the data warehouse, the workspace manager file system providing the first application programming interface access to the gene expression data within the data warehouse.

10. The platform of claim 9, wherein the workspace manager file system stores gene and sample identifiers and parameters of saved analysis methods.

11. The platform of claim 10, wherein the workspace manager file system includes XML data files.

12. The platform of claim 11, wherein the XML data files have binary file attachments containing the gene expression data.

13. The platform of claim 9, wherein the workspace manager file system comprises a directory system of files and folders.

14. The platform of claim 9, wherein the workspace file manager system enforces permissions to the gene expression data.

15. The platform of claim 1, wherein the workspace manager file system comprising:
   a data object comprising the gene expression data stored in an application specific binary format;
   an XML descriptor containing descriptive information concerning the gene expression data with the data object, wherein the data object serves as an attachment to the XML descriptor; and
   further comprising directory information for locating the data object within the data warehouse.

16. The platform of claim 15, wherein the XML descriptor includes one or more data type selected from the group consisting of ownership data, permissions data, gene chip set data and data object name.

17. The platform of claim 16, wherein the data object name comprises a tag for the binary object data, the tag representing a unique data object name.

18. The platform of claim 1, further comprising a Java interface for providing access to the gene expression data.

19. The platform as set forth in claim 1, further comprising a R interface for providing access to the gene expression data.

20. The platform as set forth in claim 1, further comprising a Perl interface for providing access to the gene expression data.

21. The platform of claim 1, wherein the portion of the gene expression data stored within the run time engine memory mapped files is regularly updated during off-hours using data in the data warehouse.

22. A platform comprising a processor executing a program for analyzing gene expression data, wherein the platform comprising:
   a data warehouse comprising a plurality of databases for storing gene expression data, sample data that corresponds to the gene expression data, and gene index data that identifies the gene expression data, wherein the plurality of databases are integrated into a relational database having a relational database management system for managing data flow to and from the data warehouse;

a run time engine receiving gene expression data from the data warehouse by means of the relational database management system; storing the received gene expression data in the form of core and derived gene expression data arranged in a matrix of absent/present calls and intensities or expression values for each sample/gene pair in memory mapped files in a workspace file system; wherein the run time engine comprising a plurality of analysis tools that accesses and analyzes the core and derived gene expression data in the memory mapped files in the workspace file system using a low level code, without directly accessing the relational database management system;

a matrix manager disposed between the data warehouse and the run time engine copying and refreshing the core and derived data into the matrix by creating a union of matrices from two sets of data;

a first application programming interface for accessing gene expression data, the first interface comprising a low-level interface providing direct access to individual core and derived gene expression data in the memory mapped files;

a workspace manager connected to the run time engine by means of the first application programming interface providing the first application programming interface access to the gene expression data stored in the workspace file system, wherein the workspace file system stores a plurality of data objects, each data object comprising an XML descriptor and binary attachments for the gene expression data;

a user interface to the plurality of analysis tools for entry of analysis queries and output of query responses;

a second application programming interface coupled between the user interface and the first application programming interface transferring analysis queries to the first application programming interface, wherein the second application programming interface comprises a high-level interface to the run time engine; and a display outputting one or more gene signatures, gene signature graphs, fold change, and ENortherns generated from the analysis of core and derived gene expression data from the run time engine.

23. The platform of claim 22, wherein each data object comprises the gene expression data stored in an application-specific binary format;

the XML descriptor contains descriptive information concerning the gene expression data within the data object, wherein the data object serves as an attachment to the XML descriptor; and further comprising directory information for locating the data object within a data warehouse.

24. The platform of claim 22, wherein the workspace manager file system stores gene and sample identifiers and parameters of saved analysis methods.

25. The platform of claim 22, wherein the workspace manager file system includes XML data files.

26. The platform of claim 25, wherein the XML data files have binary file attachments containing the gene expression data.

27. The platform of claim 22, wherein the portion of the gene expression data stored within the run time engine memory mapped files is regularly updated during off-hours using data in the data warehouse.

* * * * *